(12) United States Patent
Latini et al.

(10) Patent No.: US 7,550,269 B2
(45) Date of Patent: Jun. 23, 2009

(54) PTX3 AS AN EARLY PROGNOSTIC INDICATOR OF CARDIOVASCULAR AND CEREBROVASCULAR PATHOLOGIES

(76) Inventors: Roberto Latini, Via Eritrea, 62, Milano (IT) 20157; Giuseppi Peri, Via Eritrea, 62, Milano (IT) 20157; Alberto Mantovani, Via Mangiagalli, 31, Milano (IT) 20133; Aldo P. Maggioni, Via Lamarmora, 34, Firenze (IT) 50121

( * ) Notice: Subject to any disclaimer, the term of this patent is extended or adjusted under 35 U.S.C. 154(b) by 79 days.

(21) Appl. No.: 11/508,960

(22) Filed: Aug. 24, 2006

(65) Prior Publication Data

US 2006/0286617 A1    Dec. 21, 2006

Related U.S. Application Data

(63) Continuation of application No. 10/697,016, filed on Oct. 31, 2003, now abandoned.

(60) Provisional application No. 60/422,478, filed on Oct. 31, 2002.

(51) Int. Cl.
*G01N 33/53* (2006.01)
(52) U.S. Cl. .................. 435/7.1; 435/7.2; 435/7.91; 435/7.92
(58) Field of Classification Search ................ 435/7.1, 435/7.2, 7.92, 6, 91.2
See application file for complete search history.

(56) References Cited

U.S. PATENT DOCUMENTS 4,208,479 A * 6/1980 Zuk et al. ................. 435/7.9

OTHER PUBLICATIONS

Circulation 2000, vol. 102, p. 636 by Peri et al.

* cited by examiner

*Primary Examiner*—Mark L Shibuya
*Assistant Examiner*—Jacob Cheu
(74) *Attorney, Agent, or Firm*—Young & Thompson

(57) ABSTRACT

A method for the early determination of the risk of death or heart failure in infarction patients, and the risk of death, relapse or complications in ictus patients, the method being based on the determination of PTX3 from plasma or blood.

7 Claims, 4 Drawing Sheets

PTX3 AS AN EARLY PROGNOSTIC INDICATOR OF CARDIOVASCULAR AND CEREBROVASCULAR PATHOLOGIES

The present invention regards the use of PTX3 as a prognostic marker in cardiovascular and cerebrovascular diseases. More specifically the invention is directed to a method for the early evaluation of the risk of death or heart failure in myocardial infarction patients, and of the risk of death, relapse or complications in cerebral ictus patients, the method being based on the determination of PTX3 form plasma or blood.

BACKGROUND OF THE INVENTION

Pentraxin PTX3 consists of two structural domains, a N-terminal domain unrelated to any known molecule, and a C-terminal domain similar to that of the short pentraxins such as C-reactive protein (CRP) (Bottazzi et al., J. Biol. Chem. 1997; 272: 32817-32823). A substantial similarity has been found between human PTX3 (hPTX3) and animal PTX3s. To date, the biological function of PTX3 has not yet been fully understood, although PTX3 was the first member of the long pentraxin family to be cloned (Breviario et al., J. Biol. Chem. 1992; 267: 22190-22197).

The carboxyl half-domain of PTX3 aligns with the full-length sequence of CRP and SAP, whereas the NH2-terminal part of the protein does not show any significant homology with other known proteins. PTX3 recognizes and binds structures different from those recognized by CRP and SAP (Mantovani et al., PTX3/TSG6; The Cytokine Handbook in press). In contrast to short pentraxins, PTX3 is produced by various cell types, including endothelial cells, monocytes and macrophages (Vouret-Craviari et al., Infect. Immun. 1997; 65: 1343-1350). mononuclear phagocytes (Vidal Alles et al., Blood 1994; 84: 3483-3493), in response to primary inflammation-mediators such as Interleukin-1 β (IL-1β), tumor necrosis factor α (TNF-α), bacterial products, and others (Basile et al., J. Biol. Chem. 1997; 272: 8172-8178). The inoculation of these molecules in mice induces high levels of PTX3 expression in heart and skeletal muscles (Introna et al., Blood 1996; 87:1862-1872).

Recent studies have demonstrated that PTX3 is increased in patients with acute or chronic inflammatory diseases such as sepsis and myocardial infarction, but no correlation has been so far demonstrated between PTX3 and the prognosis of such diseases, or the risk associated therewith. In particular, PTX3 did not prove an independent predictor of infective-state progression in sepsis (Müiller et al., J. Leukoc. Biol. 2002; 72: 643-649). An important study has been carried out by Peri et al. (Circulation 2000; 102: 636-641) on 37 patients with acute myocardial infarction. The levels of PTX3 increased in infarcted patients, peaking at 6.94±11.26 ng/ml (mean±standard deviation) 7.5 hours after admittance at the hospital coronary units. In this study PTX3 was not associated with any risk factor, apart from patient's age.

DESCRIPTION OF THE INVENTION

Studies carried out on a large number of patients demonstrated that high blood PTX3 levels detected one day after the acute infarction episode are associated with an increased risk of death or of developing symptomatic heart failure within the following three months. Importantly, PTX3 resulted a prognostic factor independent either from the clinical, laboratory and demographic variables used to evaluate the risk to which an infarction patient is exposed, or from CRP, another protein of the same family as PTX3.

Furthermore, preliminary studies carried out on ictus patients revealed a significant increase of PTX3 which is proportional to the damage on the central nervous system.

The fact that PTX3 does not correlate with CRP short pentraxin levels and therefore represents a CRP-independent prognostic factor in myocardial infarction, is particularly important.

Accordingly, object of the present invention is a method for determining the prognosis of a patient with myocardial infarction or ictus, which comprises measuring the PTX3 plasmatic concentration and comparing it with a reference concentration, that will generally be equal to or higher than the average PTX3 concentration found in healthy subjects, whereby increased levels of plasmatic PTX3 in the myocardial infarction patient indicate an increased risk of death or heart failure, while increased levels of plasmatic PTX3 in the cerebral ictus patient indicate an increased risk of death or complications.

The plasmatic levels of PTX3 can be detected by means of any conventional immunoassay. A typical immunoassay may comprise the following steps: 1) contacting a blood or plasma sample with a monoclonal or polyclonal antibody against pentraxin, and 2) determining the specific antigen/antibody binding. The latter can be detected with both radioisotopic and non-radioisotopic methods, including for example IRMA techniques (Immune Radioimmunometric Assay), EIA (Enzyme Immuno Assay), ELISA (Enzyme Linked ImmunoSorbent Assay), FIA (Fluorescent Immuno Assay), CLIA (Chemioluminescent Immune Assay). Suitable detection means utilize radionuclides, enzymes, coenzymes, fluorophores, chemiluminescent agents, chromogens, substrates, cofactors or enzymatic inhibitors, production of free radicals, dyes and the like. According to a preferred embodiment, the assay is an ELISA utilizing the rat monoclonal antibody MNB4 (IgG2a), which is able to specifically bind PTX3 with a sensibility lower than 100 pg/ml, and a rabbit polyclonal antibody against PTX3 for detecting the bound protein.

In a further aspect the invention provides a kit for carrying out the prognostic method of the invention, consisting of a combination of reagents in defined quantities. Typically the kit will contain anti-PTX3 antibodies suitably marked, the PTX3 molecule, detection reagents and optionally buffers, diluents, stabilizers and other reagents useful for carrying out the immunoassay, in the same or separate containers.

The provision of a method for the early determination of either the risk of death or the risk of developing heart failure after myocardial infarction, and for the early determination of the risk of death or complications after cerebral ictus, advantageously allows to immediately start a therapeutic protocol in patients with unfavorable prognosis, for example by administering Angiotensin II Conversion Enzyme (ACE) inhibitors the first day after acute myocardial infarction. The validity of this therapeutic approach has been demonstrated by two large-scale mortality studies, GISSI-3 and ISIS-4, involving more than 60000 infarction patients.

The following examples illustrate the invention in greater detail.

EXAMPLE 1

Determination of PTX3 Concentration

Materials

The monoclonal antibody was obtained from a recombinant PTX3-immunized mouse spleen fused to a SP2/O murine mieloma, whereas the polyclonal serum used for protein detection was obtained from a rabbit repeatedly inoculated with PTX3.

Protocol

100 µl of a solution ("binding buffer") of 700 ng/ml MNB4 monoclonal antibody were placed in each well of a 96-well flat-bottomed ELISA plate (NUNC) and incubated overnight at 4° C.

After incubation, plates are washed three times with 300 µl/well of washing buffer, then each well is added with 300 µl of washing buffer containing 5% milk powder.

After 2 hr incubation at room temperature plates are washed three times with washing buffer, thereafter the standards and samples are added.

The calibration curve is prepared starting from 2.4 ng/ml of purified recombinant PTX3 in DMEM with 2% bovine serum albumin, by subsequent 2-fold dilution up to a final concentration of 75 pg/ml. Each well is added with 50 µl of any concentration in triplicate. Similarly, test samples are subsequently two-fold diluted with DMEM+2% BSA and added to each well (50 µl).

After 2 hour incubation at 37° C., the plates are washed 5 times with washing buffer and the wells are added with 100 µl of purified biotinylated anti-PTX3 rabbit immunoglobulins at a final concentration of 1 µg/ml. After 1 hr at 37° C. the plates are washed 5 times and the wells are added with peroxidase-conjugated streptavidin (100 µl). The plates are incubated at 37° C. for 1 hr and washed 5 times with washing buffer. For the detection, each well is added with 100 µl chromogen and 15 min later the plates are read at 405 nm with an automatic plate-reader.

EXAMPLE 2

Clinical Study

The patients (No.: 748) admitted to the Coronary Units of 59 Italian hospitals involved in the LATIN study, not later than 12 hours from the initial symptoms, were selected on a case-control basis with a 1:1 ratio. The cases comprised patients who died during the two months following infarction and patients affected by a new ischemic or symptomatic heart failure episode. The control patients, matched for age and sex, did not experience negative events during the follow-up.

PTX3 and CRP were assayed in plasma collected at entry (two samples for each patient) and the following morning.

Results

The PTX3 mean concentration detected during a 24 hour period after acute myocardial infarction in the controls was 7.08 ng/ml, while it increased two-fold (p<0.001) in patients (cases) who developed heart failure or died during a three month period following the initial infarction episode. No increase of PTX3 concentration was observed in patients with cardiovascular ischemia. CRP showed a similar trend. PTX3 and CRP concentrations were not correlated to each other. Multivariate (logistic) analysis showed that both PTX3 and CRP were independent predictors of mortality or heart failure in a three month period after infarction. In particular, patients with a PTX3 concentration higher than 11.2 ng/ml (upper tertile) had a mortality risk 3.85 fold (95% confidence interval: 1.47-10.07) higher than patients in the lower tertile (<=5.6 ng/ml). Similar results were obtained in connection with the heart failure risk.

In conclusion, PTX3 has been shown for the first time to be a predictor of death and heart failure after myocardial infarction, independent of main clinical/instrumental risk indicators after myocardial infarction (e.g. age, Killip class at entry, cardiac frequency, serum creatine kinase, site of the infarction) and of CRP.

Figure 1:
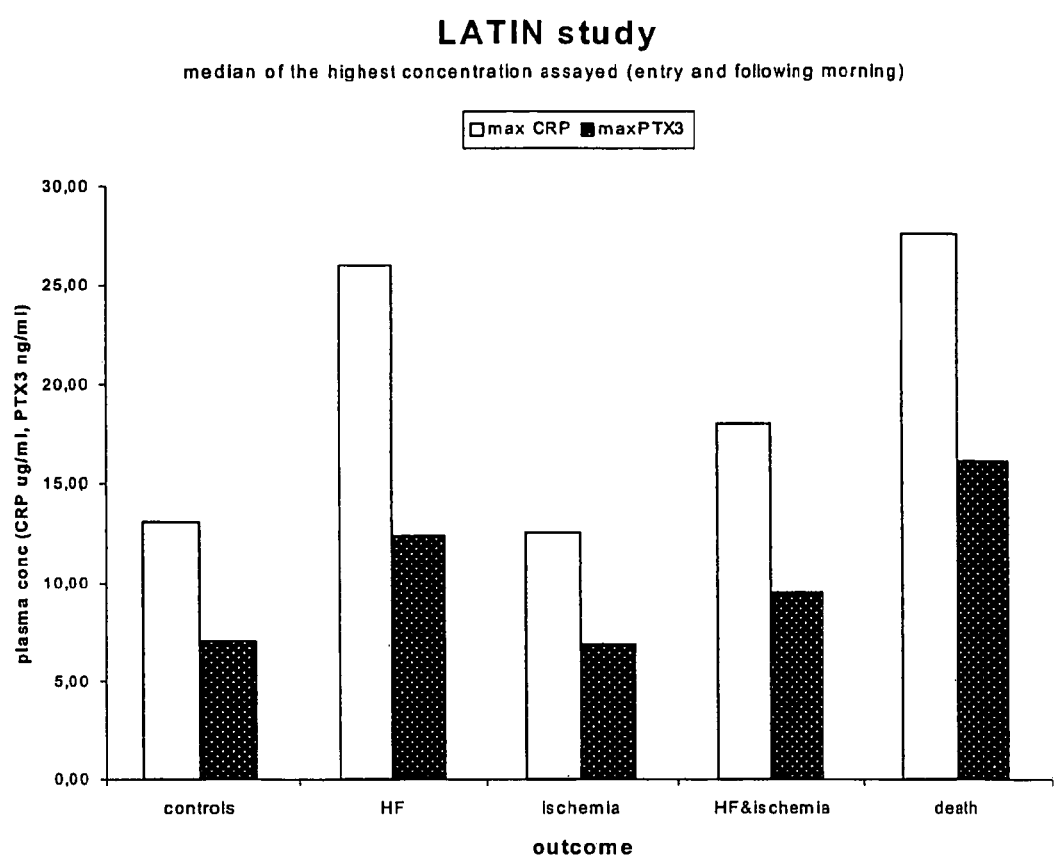
FIG. 1. median of the highest PTX3 and CRP concentrations in acute myocardial infarction patients enrolled in the LATIN study—result of a 3-month period.
Figure 2:
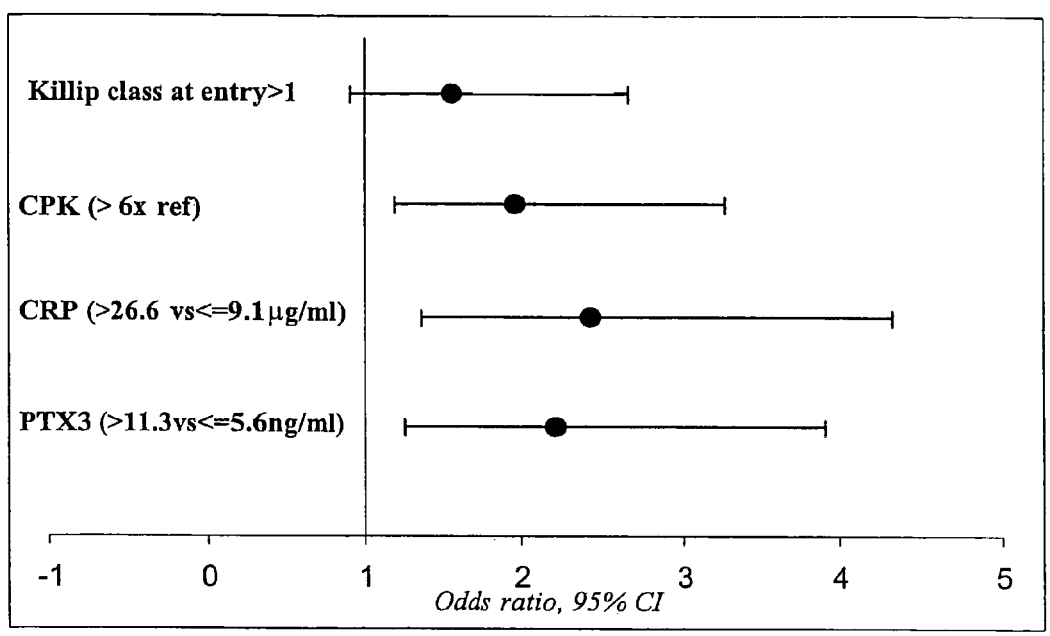
FIG. 2. Prognostic factors (represented as the odds ratio, 95% confidence interval) for mortality after acute myocardial infarction, calculated with a multivariate Cox model.
Figure 3:
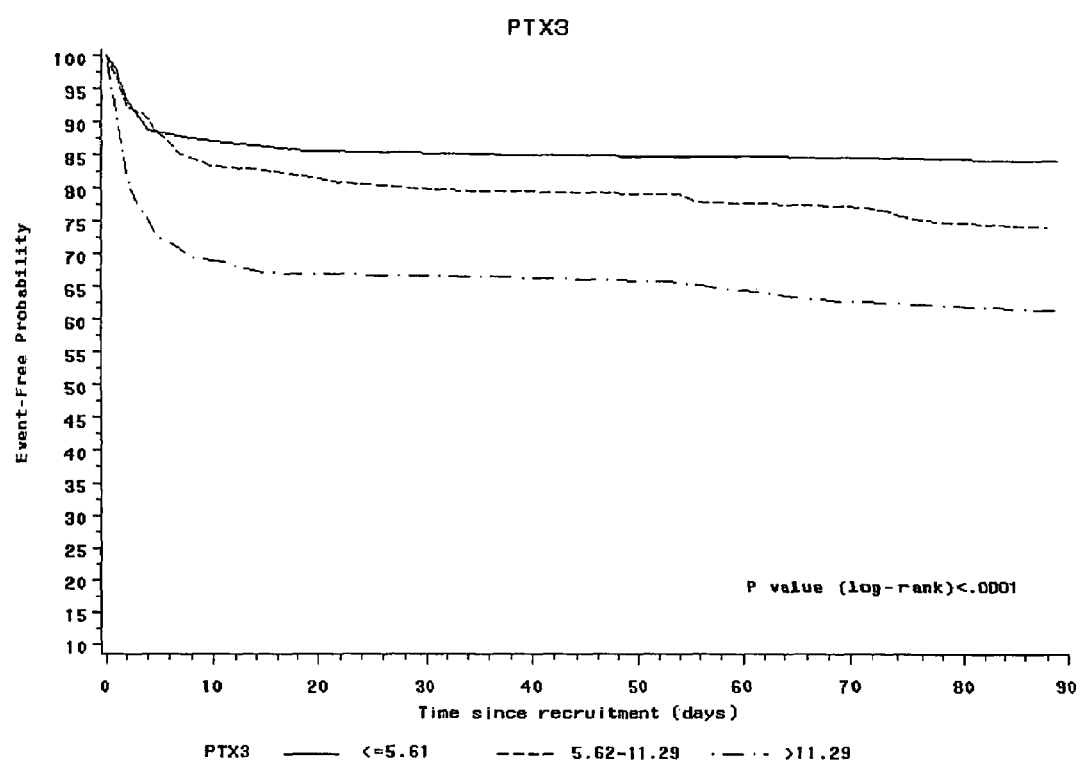
FIG. 3. Kaplan-Meier analysis for combined death endpoint or heart failure in acute myocardial infarction patients enrolled in the LATIN study, divided by PTX3 levels in the first day (the tertile limits expressed in ng/ml are reported in the bottom).
Figure 4:
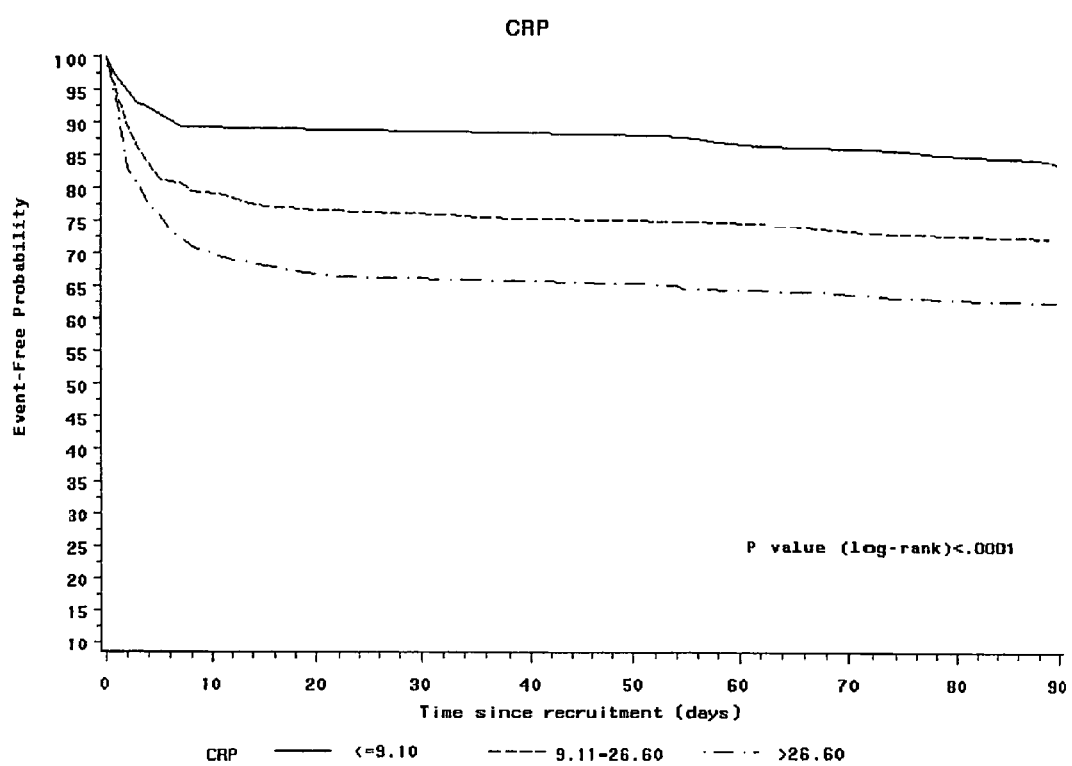
FIG. 4. Kaplan-Meier analysis for combined death endpoint or heart failure in acute myocardial infarction patients enrolled in the LATIN study, divided by CRP levels in the first day (the tertile limits expressed in ng/ml are reported in the bottom).

The invention claimed is:

1. A method for the prognosis of myocardial infarction patients, comprising:
   a) providing a blood or plasma sample from a myocardial infarction patient;
   b) measuring the concentration of pentraxin (PTX3) in the sample;
   c) comparing the PTX3 concentration in the samples with a reference PTX3 concentration value of 11.2 ng/ml, wherein an increased PTX3 concentration in the sample from the myocardial infarction patient compared with the reference PTX3 concentration, is an indicator of increased risk of death or heart failure.

2. The method according to claim 1, wherein the PTX3 concentration is determined by means of an immunoassay.

3. The method according to claim 2, wherein said immunoassay is an ELISA.

4. The method according to claim 1, wherein the prognosis is for the early determination of the risk of death or heart failure in a myocardial infarction patient.

5. The method according to claim 4, wherein the PTX3 concentration is determined within 24 hours from the myocardial infarction.

6. A kit for carrying out the method of claim 1, containing anti-PTX3 antibodies, the PTX3 molecule and detection reagents in the same or separate containers.

7. A method for the prognosis of myocardial infarction patients, comprising:
   a) providing a blood or plasma sample from a myocardial infarction patient;
   b) measuring the concentration of pentraxin (PTX3) in the sample;
   c) comparing the PTX3 concentration in the samples with a reference PTX3 concentration value of 7.08-11.2 ng/ml, wherein an increased PTX3 concentration in the sample from the myocardial infarction patient compared with the reference PTX3 concentration, is an indicator of increased risk of death or heart failure.

* * * * *